United States Patent [19]

Michaud et al.

[11] Patent Number: 4,492,679
[45] Date of Patent: Jan. 8, 1985

[54] CYANURIC CHLORIDE HAVING IMPROVED SHELF LIFE

[75] Inventors: Horst Michaud, Trostberg; Joachim von Seyerl, Seeon, both of Fed. Rep. of Germany

[73] Assignee: SKW Trostberg Aktiengesellschaft, Trostberg, Fed. Rep. of Germany

[21] Appl. No.: 516,260

[22] Filed: Jul. 22, 1983

[30] Foreign Application Priority Data

Aug. 3, 1982 [DE] Fed. Rep. of Germany ....... 3228915

[51] Int. Cl.³ .............................................. C01C 3/08
[52] U.S. Cl. ..................................... 423/268; 423/371
[58] Field of Search ....................... 423/268, 371, 383

[56] References Cited

U.S. PATENT DOCUMENTS

| 2,920,937 | 1/1960 | Burns | 423/268 |
| 3,186,828 | 6/1965 | Baarson et al. | 423/268 |
| 4,329,325 | 5/1982 | Vollbrecht et al. | 423/371 |

FOREIGN PATENT DOCUMENTS 256409  5/1963  Australia ............ 423/383

Primary Examiner—John Doll
Assistant Examiner—Wayne A. Langel
Attorney, Agent, or Firm—Felfe & Lynch

[57] ABSTRACT

A cyanuric chloride of improved shelf life is described, which contains 0.1 to 10% of dicyandiamide by weight. The cyanuric chloride of the invention shows both a decidedly lesser tendency to cake up and an improved resistance to hydrolysis in the presence of moisture.

9 Claims, No Drawings

CYANURIC CHLORIDE HAVING IMPROVED SHELF LIFE

The present invention relates to a cyanuric chloride of improved shelf life in regard to its tendency to cake and to become hydrolyzed in the presence of moisture.

Cyanuric chloride, (2,4,6-trichlor-1,3,5-triazine) is an important intermediate for the production of numerous chemical compounds which are usable, for example, as plant protection agents, dyes, optical brighteners, pharmaceuticals and textile and rubber-making adjuvants. A particular disadvantage in the handling and storage of cyanuric chloride is its tendency to cake and to hydrolyze, causing corrosive and health-harmful hydrochloric acid vapors to be released. Since, however, it is essential to comminute this material for further processing, special precautions must be taken to protect endangered persons. There has been no lack of attempts to eliminate these disadvantages of cyanuric chloride by means of some kind of additives.

It is known, for example, to use basic amines as acid-binding agents for the hydrochloric acid that forms in accordance with the equation (1):

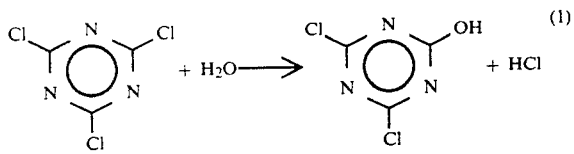

A disadvantage of these basic amines, however, is that, on account of their basicity, they themselves initiate the production of hydrochloric acid, and, because they are nucleophilic, they react with cyanuric chloride to yield hydrochloric acid.

The addition of tricalcium phosphate is known from U.S. Pat. No. 4,268,408, and the addition of pyrogenic silica, which is sold under the name of "Aerosil", is known from U.S. Pat. No. 3,141,881, for the purpose of improving the flowing characteristics and reducing the caking tendency of cyanide chloride. Both of these substances do prevent the caking of cyanuric chloride, but they cannot satisfactorily prevent the "smoking" of the cyanuric chloride due to the splitting off of HCl in the presence of moisture.

It is therefore the object of the invention to develop a cyanuric chloride of improved shelf life, which is substantially improved as regards hydrolysis in the presence of moisture and as regards caking, without great technical and financial investment.

This object is achieved in accordance with the invention by a cyanuric chloride which contains from 0.1 to 10% of finely divided dicyandiamide by weight. For it has surprisingly been found that the addition of dicyandiamide suppresses the development of hydrochloric acid vapors, even though dicyandiamide is a solid which has a neutral reaction in water and thus is hardly a base. Especially surprising, therefore, is the improvement of flow qualities, since dicyandiamide itself, as it is commonly known, tends to cake. Elimination of the tendency to cake by combining two substances which tend to cake must therefore be considered as a synergistic effect.

The cyanuric chloride of the invention can be prepared by the addition of 0.1 to 10%, preferably 1 to 5%, by weight, of dicyandiamide, by the mixing method commonly practiced in the art. The dicyandiamide should be in finely divided form with a grain size between 1 and 100 microns. The addition of the dicyandiamide during the gas phase desublimation of the cyanuric chloride has proven to be especially advantageous, because then the dicyandiamide can be added in an especially simple manner by blowing it into the cyanuric chloride.

Another advantage of the invention is that dicyandiamide is inert both with respect to cyanuric chloride and with respect to water, and therefore the synthesis of secondary products can be performed without problems.

The following examples are to further explain the invention without limiting the invention thereto.

EXAMPLE 1

Cyanuric chloride was carefully mixed with 1 wt.-% of dicyandiamide and stored for two months at room temperature. After the storage container was opened, no HCl odor was detected, in contrast to a comparative test sample. Blowing moist air across a sample produced no fog.

EXAMPLE 2

Cyanuric chloride was carefully mixed with 5 wt.-% of dicyandiamide and stored for 4 weeks at room temperature. Whereas a comparative test sample was caked up, the sample to which dicyandimide was added could easily be shaken up.

EXAMPLE 3

Cyanuric chloride, which had been mixed with 0.5 wt.-% of ground dicyandiamide and stored for one week at room temperature, produced no HCl fog when the storage vessel was opened. In a comparative sample, however, a strong development of HCl was encountered.

We claim:

1. Cyanuric chloride having improved shelf life, comprising cyanuric chloride and 0.1-10 percent by weight of dicyandiamide.

2. The cyanuric chloride of claim 1 comprising 1-5 percent by weight of the dicyandiamide.

3. The cyanuric chloride of claim 1 wherein the dicyandiamide has a grain size of 1-100 microns.

4. The cyanuric chloride composition of claim 2 wherein the dicyandiamide has a grain size of 1-100 microns.

5. Method of preparing cyanuric chloride of improved shelf life comprising the steps of mixing the cyanuric chloride with 0.1 to 10 percent by weight of dicyandiamide in finely divided form.

6. The method of claim 5 wherein dicyandiamide of a grain size of 1 to 100 microns is used.

7. The method of claim 5 wherein the dicyandiamide is added during a gas phase desublimation of the cyanuric chloride.

8. The method of claim 6 wherein the dicyandiamide is added during a gas phase desublimation of the cyanuric chloride.

9. The method of claim 5 wherein 1-5 percent by weight of dicyandiamide is used.